United States Patent

Ripa et al.

[11] Patent Number: 5,886,174
[45] Date of Patent: Mar. 23, 1999

[54] PROCESS FOR THE PREPARATION OF 1,4,7, 10-TETRAAZACYCLODODECANE

[75] Inventors: Giorgio Ripa; Maria Argese, both of Milan, Italy

[73] Assignee: Dibra S.p.A., Italy

[21] Appl. No.: 66,714

[22] Filed: Apr. 27, 1998

[30] Foreign Application Priority Data

Apr. 28, 1997 [IT] Italy .................................. MI97A0982

[51] Int. Cl.$^6$ .................................................. C07D 257/02
[52] U.S. Cl. ...................... 540/474; 544/343; 548/301.7; 548/302.1
[58] Field of Search .............................. 540/474; 544/343

[56] References Cited

U.S. PATENT DOCUMENTS

| 5,434,262 | 7/1995 | Guilard et al. | 540/474 |
| 5,587,451 | 12/1996 | Athey et al. | 528/345 |
| 5,589,595 | 12/1996 | Sandnes et al. | 540/474 |

FOREIGN PATENT DOCUMENTS

| 02987 | 6/1997 | European Pat. Off. . |
| 02222 | 4/1998 | European Pat. Off. . |
| 97/49691 | 12/1997 | WIPO . |

*Primary Examiner*—Mukund J. Shah
*Assistant Examiner*—Pavanaram K Sripada
*Attorney, Agent, or Firm*—Nixon & Vanderhye

[57] ABSTRACT

A process for the preparation of 1,4,7,10-tetraazacyclododecane of formula (I), starting from decahydro-2a,4a,6a,8a-tetraazacyclopent[fg]acenaphthylene of formula (II):

comprising the direct step of hydrolysis in aqueous solution, in conditions of slightly acid, neutral or slightly basic pH, with a primary diamine of formula (V), in which x ranges between 0 and 2, and Q is —$CH_2CH(OH)CH_2$—, —$(CH_2)_2NH(CH_2)_2$—, or —$[(CH_2)_2NH]_2(CH_2)_2$, when x is 1, or Q is —$CH_2$— when x is 2.

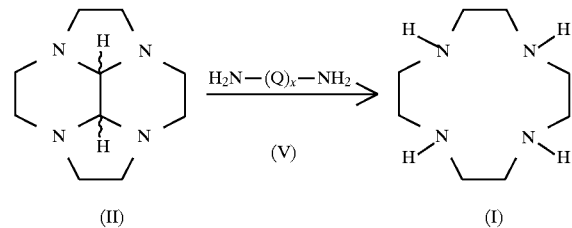

9 Claims, No Drawings

PROCESS FOR THE PREPARATION OF 1,4,7, 10-TETRAAZACYCLODODECANE

The present invention relates to a process for the preparation of 1,4,7,10-tetraazacyclododecane (I) starting from decahydro-2a,4a,6a,8a-tetraazacyclopent-[fg] acenaphthylene (II):

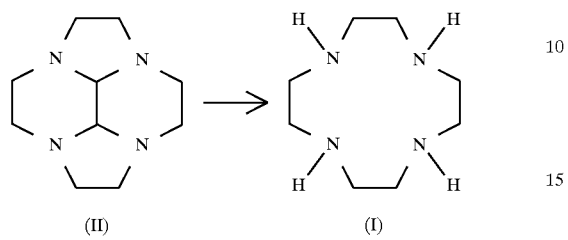

The compound of formula (II) can be prepared by cyclization of the intermediate (III), octahydro-3H,6H-2a,5, 6,8a-tetraazacenaphthylene, which can in its turn be prepared from triethylenetetramine and glyoxal, as disclosed in International Patent application WO 97/49691 and in Italian Patent application MI96A001257, or from two moles of ethylenediamine through the intermediate of formula (IV), according to the following scheme:

Scheme 1

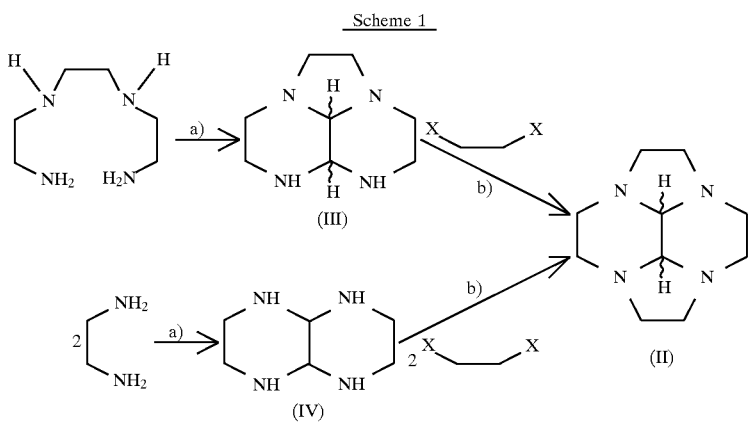

in which step a) represents the condensation step of triethylenetetramine (or ethylenediamine) with glyoxal, in water or in water-soluble solvents or in mixtures thereof, at a temperature ranging from 0° to 50° C., in the presence of stoichiometric amounts or slight excesses of calcium hydroxide, to give the compound of formula (III) or (IV); and step b) represents, on the other hand, the condensation of the compound of formula (III) or (IV) with an alkylating agent X—(CH$_2$)$_2$—X, in which X is a halogen or a sulfonic acid reactive derivative, in at least stoichiometric amounts, in the presence of at least 2 moles of a base selected from alkali or alkaline-earth metal carbonates per mole of compound (III), at a temperature of 25°–150° C., to give the compound of formula (II).

The intermediate (II) has a remarkable stability in hydrolytic conditions, contrary to the common diaminals which are easily hydrolyzed:

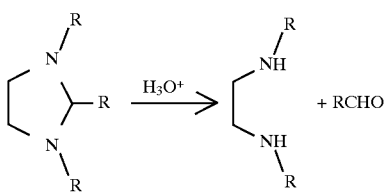

For example, publications by Weisman (Tetrahedron Lett., 1980, 21, 335) and by Kolinski (Tetrahedron Lett., 1981, 22, 2217), concerning the synthesis of (II) starting from (I) and glyoxal, confirm the exceptional stability of (II) to acid or basic hydrolytic conditions as well as to reducing agents.

In order to cleave the two carbon atom-bridge which characterizes (II), therefore to obtain (I), an oxidizing process has been described in the already cited Italian Patent application MI96A001257, which allows to transform (II) into oxidation products which can subsequently be transformed into (I) by basic hydrolysis. The whole process from (II) to (I), described in MI96A001257, consists of two steps:

1) oxidation of (II)

2) hydrolysis of the products from the oxidation of (II)

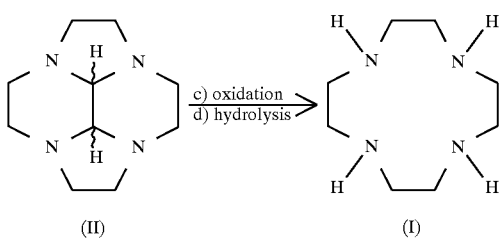

Alternatively to the oxidative cleavage, WO96/28432 suggests the direct hydrolysis of (II) with hydrobromic acid, or with hydroxylamine in ethanol solution under reflux.

Hydrolysis treatment with hydrobromic acid, not exemplified in WO96/28432, is apparently in disagreement with the teachings of literature, which point out the unexpected stability of compound of formula (II) in acid or basic aqueous solutions.

On the other hand, the reaction with hydroxylamine requires strong excesses of the latter (10 eq. mol) as a free base in ethanol under reflux.

These conditions, although acceptable on laboratory scale, are however not very useful for the industrial processes, as hydroxylamine is quite dangerous (specially when hot) and requires careful handling, use and discharge.

Hydrolysis conditions for (II) which are as selective as possible and, at the same time, the simplest and most cost-saving, should therefore be found to improve the process for the preparation of (I) via (II).

Now it has surprisingly been found, and this is the object of the present invention, a process for the preparation of (I) starting from (II), comprising a hydrolysis step in aqueous solution, in conditions of slightly acid, neutral or slightly basic pH, with a primary diamine of formula (V), as represented in the following Scheme:

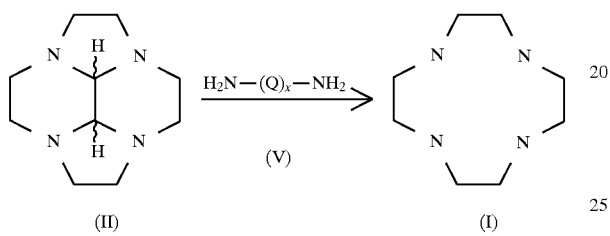

in which
x ranges between 0 and 2, and
Q is —CH$_2$CH(OH)CH$_2$—, or —(CH$_2$)$_2$NH(CH$_2$)$_2$—, or —[(CH$_2$)$_2$NH]$_2$(CH$_2$)$_2$, when x is 1, or
Q is —CH$_2$— when x is 2.

In the general formula, x can be 0, 1 or 2. In the first case, the diamine corresponds to hydrazine.

In the other cases, the nature of the diamine depends on the nature of Q, as schematized in the following:

| x | Q | Diamine |
|---|---|---|
| 0 | — | Hydrazine |
| 1 | —CH$_2$CH(OH)CH$_2$— | 1,3-Diamino-2-propanol |
| 1 | —(CH$_2$)$_2$NH(CH$_2$)$_2$— | Diethylenetriamine |
| 1 | [(CH$_2$)$_2$NH$_2$(CH$_2$)$_2$]$_2$ | Triethylenetetramine |
| 2 | —CH$_2$— | Ethylenediamine |

The reaction is extremely selective, allowing not only to obtain high quality (I) in good yields, by also to recycle, in some cases, the reaction by-products, as they can easily be retransformed into (II).

The reaction takes place in water, in a pH range from 5.5 to 9, preferably from 6 to 8, at temperatures from 60° to 150° C., preferably 60° to 100° C., in the presence of 2–20 mol of diamine per mol of (II), at normal pressure under inert gas atmosphere or in the air, for 12–48 h, or under pressure, for 3–10 h.

At the end of the reaction, the solution is alkalinized with a base, such as sodium hydroxide, concentrated to small volume or to a residue, then (I) is extracted with a suitable solvent, such as toluene, chloroform, butanol, amyl alcohol. The organic phase is concentrated to a residue, to obtain the crude macrocycle (I), which is finally recrystallized from toluene or ethyl acetate.

When the extraction solvent is toluene, it is sufficient to concentrate the toluene solution to a suitable volume, then crystallize the macrocycle (I).

Depending on the diamine used, more developed processes can be defined, providing for the recovery of the reaction by-products.

For example, in the case of triethylenetetramine, the reaction gives (I) and (III), according to the scheme below:

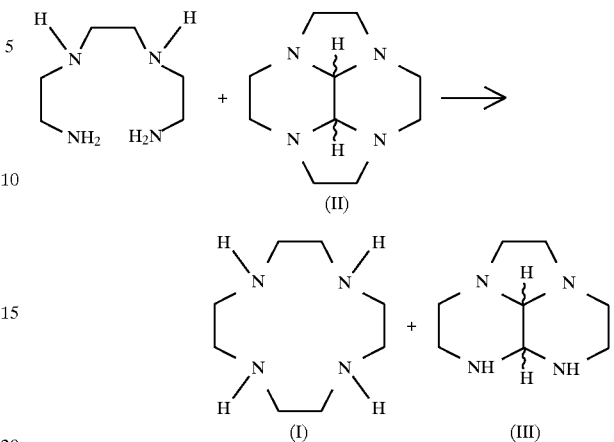

Toluene mother liquors coming from crystallization of (I), substantially containing (III) and triethylenetetramine excess, can be concentrated to a residue, which is in its turn redissolved in water and reacted with glyoxal in the conditions described in MI96A001257, so as to obtain (III), which can optionally be purified, then is transformed into (II) according to the procedure reported in MI96A001257 and finally recycled into the process.

In the case of ethylenediamine, the hydrolysis reaction of (II) also gives recyclable by-products:

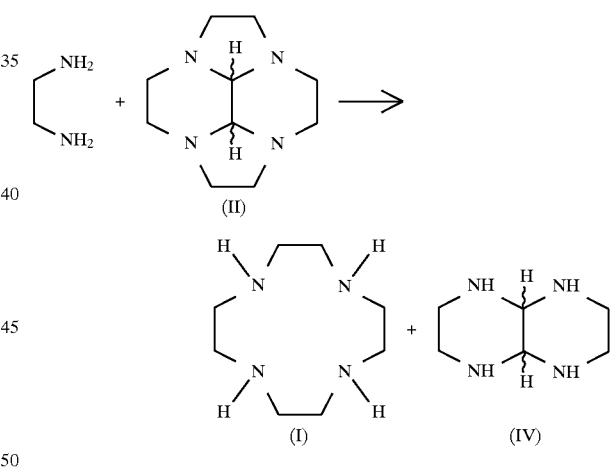

Compound (IV) can also be recovered from toluene mother liquors and retransformed into (II), as already described in MI96A001257.

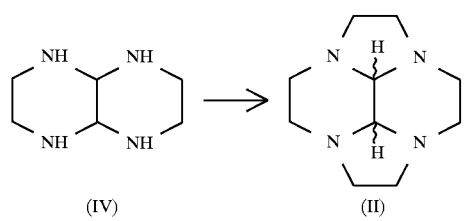

Some preparation examples according to the method of the invention are reported in the following experimental section

EXAMPLE 1

Preparation of (I) by hydrolysis of (II) with diethylenetriamine 50 g of (II) (0.257 mol) are dissolved in 350 ml of water. 132.5 g of diethylenetriamine (1.285 mol) are added and pH adjusted to 8 with conc. HCl (265 g). The resulting solution is refluxed for 24 h, then cooled, alkalinized with NaOH in pellets, concentrated under vacuum to a residual weight of 350 g and extracted (I) with toluene. The combined organic extracts are concentrated to an about 90 mL volume and left to crystallize. 31.5 g of high quality 1,4,7,10-tetraazacyclododecane are obtained (GC titre: 99.5%). Yield. 71%.

EXAMPLE 2

Hydrolysis of (II) with triethylenetetramine and recovery of the reaction by-products 50 g of (II) (0.257 mol) are dissolved in 350 ml of water. 105 g (0.640 mol) of triethylenetetramine monohydrate are added and pH is adjusted to 7.5 with conc. HCl. The resulting solution is refluxed for 18 h, then cooled, alkalinized with NaOH in pellets, concentrated under vacuum to a 330 g residual weight and repeatedly extracted with toluene. The combined organic extracts are concentrated under reduced pressure to about 120 mL and left to crystallize. 29.4 g of good quality 1,4,7,10-tetraazacyclododecane are obtained (GC Tit.: >98.5%). Yield: 66%.

Toluene mother liquors are concentrated to a residue, which is redissolved in water. The content in triethylenetetramine and in (III) is determined by GC analysis. Glyoxal and calcium hydroxide are added in amounts such as to transform triethylenetetramine into (III), according to the conditions described in MI 96A 001257. After completion of the reaction, the inorganic salts are filtered off, the filtrate is concentrated to a residue and added with hexane, any insolubles are filtered off and the solution is concentrated to dryness. 67.2 g (0.40 mol) of (III) are obtained, which can be used to prepare (II) according to the procedure described in MI 96A 001257.

EXAMPLE 3

Hydrolysis of (II) with ethylenediamine and recovery of the reaction by-products 50 g of (II) (0.257 mol) are dissolved in 300 ml of water. 157.5 g of ethylenediamine (2.57 mol) are added and pH is adjusted to 8 with conc. HCl (310 g). The resulting solution is refluxed for 18 h, then cooled, alkalinized with NaOH in pellets, concentrated under reduced pressure to 400 g and repeatedly extracted with toluene. The combined organic extracts are concentrated to a 100 mL volume and left to crystallize. 24.8 g of high quality 1,4,7,10-tetraazacyclododecane are obtained (GC titre: >99%). Yield: 56%.

Toluene mother liquors are concentrated under reduced pressure. The residue is subjected to chromatography on silica (eluent: chloroform:methanol: 25% ammonia=6:3:1). 21 g (0.148 mol) of (IV) are obtained, which can be retransformed into (II) in the conditions described in MI 96A 001257.

EXAMPLE 4

Hydrolysis of (II) with various diamines at various pH and temperatures 19.4 g (0.1 mol) of (II) are hydrolyzed with a similar procedure to that described in example 1, using the diamines and the conditions reported in the following table:

| Diamine | mol/mol (II) | pH | T (°C.) | t (h) | % Yield |
| --- | --- | --- | --- | --- | --- |
| Hydrazine | 20 | 7 | 100 | 24 | 60% |
| Hydrazine | 10 | 6.5 | 100 | 48 | 55% |
| Ethylenediamine | 10 | 6.5 | 100 | 18 | 52% |
| Ethylenediamine | 8 | 7 | 80 | 24 | 45% |
| Ethylenediamine | 10 | 5.5 | 100 | 18 | 42% |
| Diethylenetriamine | 4 | 7.5 | 80 | 24 | 58% |
| Diethylenetriamine | 6 | 6.5 | 100 | 12 | 62% |
| Diethylenetriamine | 6 | 8 | 60 | 48 | 65% |
| Triethylenetetramine | 4 | 6 | 80 | 24 | 55% |
| Triethylenetetramine | 2 | 8 | 100 | 48 | 62% |
| Triethylenetetramine | 2 | 9 | 100 | 48 | 57% |
| 1,3-Diamino-2-propanol | 6 | 7 | 100 | 24 | 51% |
| 1,3-Diamino-2-propanol | 5 | 8 | 100 | 18 | 48% |

We claim:

1. A process for the preparation of 1,4,7,10-tetraazacyclododecane of formula (I) starting from decahydro-2a,4a,6a,8a-tetraazacyclopent[fg]acenaphthylene of formula (II):

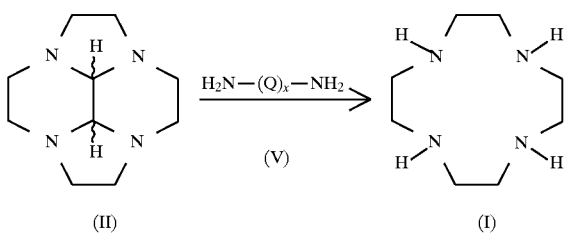

comprising a direct step of hydrolysis in aqueous solution, in conditions of slightly acid, neutral or slightly basic pH, with a primary diamine of formula (V), wherein:

x ranges between 0 and 2, and

Q is $-CH_2CH(OH)CH_2-$, or $-(CH_2)_2NH(CH_2)_2-$, or $-[(CH_2)_2NH]_2(CH_2)_2$, when x is 1, or Q is $-CH_2-$ when x is 2.

2. A process according to claim 1, in which the diamine is selected from the group of: diethylenetriamine, triethylenetetramine and ethylenediamine.

3. A process according to claim 1, in which the hydrolysis reaction is carried out in water, at a pH from 5.5 to 9, at temperatures ranging from 60° to 150° C., preferably 60° to 100° C., in the presence of 2–20 mol of diamine per mole of (II), at normal pressure under inert gas atmosphere or in the air, for 12–48 h, or under pressure, for 3–10 h.

4. A process according to claim 3, in which the reaction pH ranges from 6 to 8.

5. A process according to claim 1, in which the diamine is triethylenetetraamine, represented in the following scheme

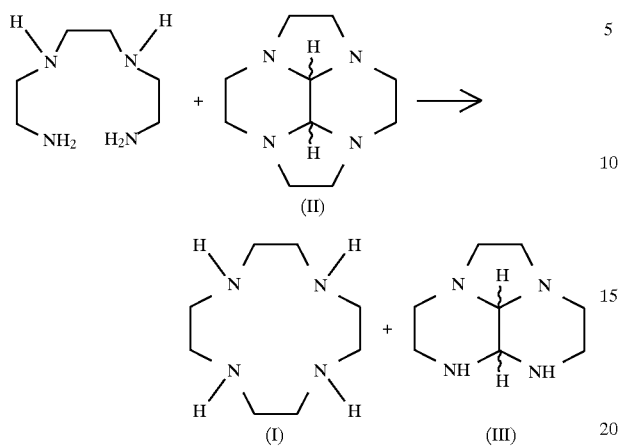

in which compound of formula (III), octahydro-3H,6H-2a, 5,6,8a-tetraazacenaphthylene, is simultaneously formed, which is an intermediate useful for, the preparation of the compound of formula (II), decahydro-2a,4a,6a,8a-tetraazacyclopent[fg]acenaphthylene, according to known methods.

6. A process according to claim 5, in which the mother liquors from the crystallization of the compound of formula (I), substantially containing the compound of formula (III) and the triethylenetetramine excess, are concentrated to a residue, which is in its turn redissolved in water and can be used as an intermediate for the preparation of the compound of formula (II), according to known methods.

7. A process according to claim 1, in which the diamine is diethylenetriamine.

8. A process according to claim 1, in which the diamine is ethylenediamine, according to the following scheme

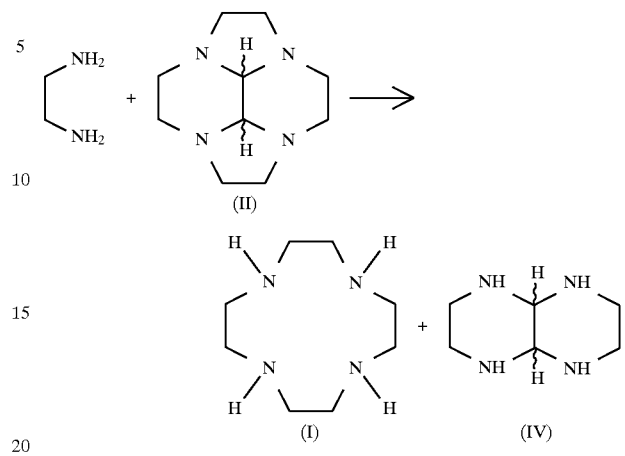

in which compound of formula (IV), decahydropyrazino[2,3-b]pyrazine, is simultaneously formed, which is an intermediate useful for the preparation of the compound of formula (II), decahydro-2a,4a,6a,8a-tetraazacyclopent[fg] acenaphthylene, according to known methods.

9. A process according to claim 8, in which the mother liquors from the crystallization of compound of formula (I), substantially containing compound of formula (IV), are concentrated to a residue, which is in its turn redissolved in water and can be used as an intermediate for the preparation of compound of formula (II), according to known methods.

\* \* \* \* \*